United States Patent [19]

Gaertner

[11] 4,094,928

[45] June 13, 1978

[54] CARBONYLALDIMINOMETHANEPHOSPHONATES

[75] Inventor: Van Russell Gaertner, Ballwin, Mo.

[73] Assignee: Monsanto Company, St. Louis, Mo.

[21] Appl. No.: 820,195

[22] Filed: Jul. 29, 1977

Related U.S. Application Data

[63] Continuation-in-part of Ser. No. 531,586, Dec. 11, 1974, abandoned.

[51] Int. Cl.$^2$ .................................................. C07F 9/40
[52] U.S. Cl. .................................. 260/944; 260/502.5
[58] Field of Search ............................. 260/502.5, 944

[56] References Cited

U.S. PATENT DOCUMENTS 3,328,391  6/1967  Sandri et al. ...................... 260/502.5

*Primary Examiner*—Anton H. Sutto
*Attorney, Agent, or Firm*—William T. Black; Donald W. Peterson

[57] ABSTRACT

Carbonylaldiminomethanephosphonates are produced by the reaction of glyoxal or glyoxylic acid esters with aminomethylphosphonic acid esters. The carbonylaldiminomethanephosphonates can then be reduced and hydrolyzed or reduced and oxidized to yield N-(phosphonomethyl)glycine which is useful as a post-emergent herbicide.

6 Claims, No Drawings

CARBONYLALDIMINOMETHANEPHOSPHONATES

This application is a continuation-in-part of U.S. application Ser. No. 531,586 filed Dec. 11, 1974, now abandoned.

This invention contemplates the production of carbonylaldiminomethanephosphonates. Carbonylaldiminomethanephosphonates are produced by the reaction of glyoxylic acid esters or glyoxal with aminomethane phosphonic acid esters. The carbonylaldiminomethanephosphonates of this invention are reduced and then hydrolyzed to N-(phosphonomethyl)glycine.

It is known that N-(phosphonomethyl)glycine can be produced by the oxidation of N-(phosphonomethyl)iminodiacetic acid either electrolytically or by chemical oxidation.

It has now been discovered that N-(phosphonomethyl)glycine can also be produced by the catalytic reduction of carbonylaldiminomethane phosphonic acid esters of this invention and subsequent hydrolysis of the esters.

In accordance with this invention, carbonylaldiminomethanephosphonates are produced by reacting an aminomethyl phosphonic acid compound of the formula

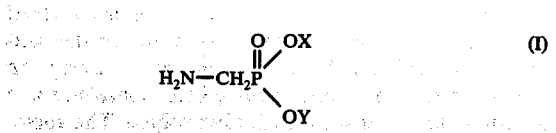

wherein X and Y are each individually hydrogen or lower alkyl groups with an aldehyde of the formula

wherein Z is hydrogen, hydroxyl or lower alkoxyl to form the carbonylaldiminomethanephosphonates of the formula

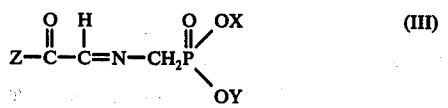

wherein X, Y and Z are as above defined.

The carbonylaldiminomethanephosphonates can then be hydrogenated to yield compounds of the formula

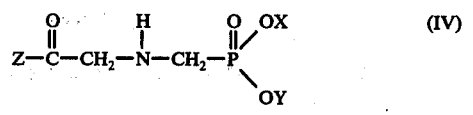

wherein X, Y and Z have the above-defined meanings.

The compounds of Formula IV are converted to N-(phosphonomethyl)glycine by the following procedure. When Z represents hydrogen, the compound is treated with an oxidizing agent either before the hydrogenation step or after said step to convert the aldehyde to a carboxylic acid. When alkoxyl groups are present, they are hydrolyzed to the hydroxyl groups employing an acid such as a hydrohalic acid, sulfuric acid or the like.

More particularly, the compounds of this invention are produced by forming an admixture of the aminomethanephosphonate and glyoxal or glyoxylic acid or ester in a solvent, heating said admixture to a temperature sufficiently elevated to initiate the condensation reaction and remove the water of reaction to form the carbonylaldiminomethanephosphonate.

The carbonylaldiminomethanephosphonate can then be oxidized if Z is hydrogen to yield a carboxyaldiminomethanephosphonate. The carbo- or carboxyaldiminomethanephosphonate can then be hydrogenated, employing hydrogen with a hydrogenation catalyst such as a noble metal catalyst, to yield N-(phosphonomethyl)glycine or its esters. Ester groups are then hydrolyzed off to yield N-(phosphonomethyl)glycine.

In conducting the initial condensation step of this invention, it is preferable to employ a solvent in which the reactants and reaction product are soluble. Solvents which can be employed are the aromatic hydrocarbons such as benzene, toluene, xylene and the like.

By the terms "lower alkyl" and "lower alkoxyl", as employed herein, is meant alkyl and alkoxyl groups containing from 1 to 5 carbon atoms. The alkyl and alkoxyl groups are, for example, methyl, ethyl, propyl, butyl, pentyl and the like and their isomers and methoxyl, ethoxyl and pentoxyl and the isomers of such alkoxyl groups. In conducting the condensation steps of this invention, it is preferred to employ the molar ratios of the glyoxal or glyoxylic acid or ester to aminomethyl phosphonate acid of at least 1 to 1. It is even more preferred to employ molar ratios of from 1.5 to 2 to 1.

In conducting the condensation step of this invention, the temperature of reaction can range from 0° C. to 140° C. or even higher. It is preferred for ease of reaction and to obtain the best rate of product to conduct the process at from about 50° C. to about 115° C. and preferably at the reflux temperature of the particular solvent being employed.

In hydrogenating the aldiminomethylene phosphonates of the invention, one can employ gaseous hydrogen and a hydrogenation catalyst, either supported on an inert carrier or as a finely divided metal catalyst such as Raney nickel, Raney Cobalt, palladium, platinum, rhodium, iridium and the like.

The amount of metal catalyst can vary over a wide range depending upon the rate of hydrogenation desired. Thus, the metal catalyst is employed in amounts of from 0.0001 to 20 or more parts by weight per 100 parts by weight of the carbonylaldiminomethanephosphonate. For ease of reaction and convenience, it is preferred to employ from .01 to .1 parts by weight of the catalyst per 100 parts by weight of the carbonylaldiminomethanephosphonate.

In conducting the hydrogenation step, the temperature can vary widely, e.g., from 0° C. to 150° C. or even higher. For convenience, it is preferred to employ temperatures in the range of from 0° C. to about 75° C. and hydrogen pressures of from 1 to 100 atmospheres or higher.

The time of reaction in the process of producing the compounds of this invention is not critical and can vary from as low as 1 minute to as high as 40 minutes or higher. It is, of course, obvious to those skilled in the art that the yield of product will vary with the reaction time and the temperature of the reaction.

The N-(phosphonomethyl)glycine which can be produced from the carbonylaldiminomethanephosphonates of this invention is useful as a post-emergent herbicide.

The following examples serve to further illustrate the invention. All parts are parts by weight unless otherwise expressly set forth.

EXAMPLE 1

To a solution of 13.0 g. (0.10 mole) of n-butyl glyoxylate in 100 ml. of toluene was added with stirring diethylaminomethylphosphonate (8.3 g., 0.05 moles) and the mixture heated to remove water of condensation by azeotropic distillation. The reaction was complete in less than 15 minutes.

The toluene was removed under vacuum in a rotary evaporator leaving an amber oil as a residue. The amber oil was distilled in a wiped wall molecular still at 150° C. to 171° C. (wall temperature) and 5–23 microns pressure. A yellow oil distillate (6.9 g.) was recovered. The yellow oil was redistilled in a Hickman molecular still (magnetically stirred) to yield a fraction b.p. 134°–137° C. at 12–13 microns $n_D^{22}$ 1.4514 which was analyzed.

Calc'd. for $C_{11}H_2NO_5P$: P = 11.09; Found: P = 11.22.

This material was identified as diethyl carbo-n-butoxyaldiminomethanephosphonate.

In a second run employing only a 25% excess of n-butyl glyoxylate, a 45% yield of a less pure product was obtained.

EXAMPLE 2

To a solution of diethyl aminomethanephosphonate (8.3 g. or 0.050 mole) in 100 ml. of toluene was added 40% aqueous glyoxal (3.6 g. or 0.025 mole). A mild exotherm was observed after which the mixture was heated to reflux and water removed by azeotropic distillation.

Removal of toluene, followed by molecular distillation in a wiped wall still at 150°–152° C. (wall temperature) and 5–29 microns pressure yielded 2.0 grams of a light yellow oil $n_D^{22}$ 1.4575, identified as diethyl formylmethyleneiminomethanephosphonate.

Cal'd. for $C_7H_{14}NO_4P$: P = 14.95%; Found: P = 15.24%.

EXAMPLE 3

The aldimino ester from Example 1 is dissolved in 5 times its volume of ethanol and 1 percent by weight of a 10% palladium on charcoal catalyst is added to the solution in a stainless steel pressure vessel. The pressure vessel is evacuated until ethanol begins to distill, then hydrogen is passed in slowly until the pressure reaches 100 psi (292.6 kilograms per square centimeter). The rocker is started and the pressure falls to a stable value. The reactor is heated to 50° C. and repressurized to 100 psi (292.6 killograms per square centimeter) until the pressure remains stable.

The reactor is cooled and vented and the solution is filtered to remove the catalyst and concentrated. The residual oil containing n-butyl N-(diethoxyphosphinylmethyl)glycinate is sufficiently pure for hydrolysis. The n-butyl N-(diethoxyphosphinylmethyl)glycinate is hydrolyzed by heating to boiling with excess concentrated hydrobromic acid, concentrating and separating the product by crystallization. The product is N-(phosphonomethyl)glycine.

EXAMPLE 4

A solution of 34 grams (0.20 mole) of silver nitrate in 100 ml. of water is treated with a solution of sodium hydroxide (16 grams) in 15 ml. of water. To this suspension of brown silver oxide is added, with cooling in small portions at 15° to 20° C., diethyl formylmethyleneiminomethanephosphonate. (20.7 grams). After stirring briefly, the solution is filtered to remove the precipitated metallic silver and the filtrate carefully acidified with dilute hydrochloric acid to a pH of 3.

Concentration of the solution and drying by azeotropic distillation with ethanol, followed by filtration to remove sodium nitrate, gives the crude unsaturated acid, diethyl carboxyaldiminomethanephosphonate.

To the above solution, is added 1 gram of 10% palladium on carbon catalyst in a stainless steel pressure vessel. The pressure vessel is sealed and evacuated until the ethanol begins to vaporize. Hydrogen is passed into the pressure vessel to a gauge reading of 100 psi (292.6 kilograms per square centimeter), the rocker is started and the reaction allowed to proceed until the pressure stabilizes. Repressurizing and heating to 50° C. completes the reaction.

The pressure vessel is vented and the mixture filtered to remove the catalyst. The filtrate is concentrated and filtered again and finally taken to dryness, leaving the crude saturated carboxylic acid which contains some ester but which is satisfactory for hydrolysis. The above acid (ester) is heated to boiling with excess 48% hydrobromic acid until hydrolysis is completed. The solution is then concentrated and crystallized to yield N-(phosphonomethyl)glycine.

What is claimed is:

1. A carbonylaldiminomethanephosphonate compound of the formula $$Z-\overset{\overset{\displaystyle O}{\|}}{C}-\overset{\overset{\displaystyle H}{|}}{C}=N-CH_2\overset{\overset{\displaystyle O}{\|}}{P}\begin{subarray}{l}OX\\OY\end{subarray}$$

wherein X and Y are each individually hydrogen or lower alkyl and Z is hydrogen, hydroxyl or lower alkoxyl.

2. A compound of claim 1 wherein X and Y are lower alkyl and Z is lower alkoxyl.

3. A compound of claim 2 wherein X and Y are ethyl and Z is a butoxy group.

4. A compound of claim 1 wherein X and Y are hydrogen and Z is hydroxyl.

5. A compound of claim 1 wherein X and Y are lower alkyl and Z is hydrogen.

6. A compound of claim 5 wherein X and Y are ethyl groups and Z is hydrogen.